United States Patent [19]

Hardman et al.

[11] Patent Number: 4,540,713
[45] Date of Patent: Sep. 10, 1985

[54] PREPARATION OF ALCOHOLS FROM SYNTHESIS GAS

[75] Inventors: Harley F. Hardman, Lyndhurst; Ronald I. Beach, Chagrin Falls, both of Ohio

[73] Assignee: The Standard Oil Company, Cleveland, Ohio

[21] Appl. No.: 639,512

[22] Filed: Aug. 7, 1984

Related U.S. Application Data

[63] Continuation of Ser. No. 503,076, Jun. 13, 1983, abandoned, which is a continuation of Ser. No. 393,829, Jun. 30, 1982, abandoned, which is a continuation of Ser. No. 54,216, Jul. 2, 1979, abandoned, which is a continuation of Ser. No. 905,703, May 15, 1978, abandoned.

[51] Int. Cl.$^3$ .............................................. L07C 27/06
[52] U.S. Cl. ......................................... 518/713; 44/56
[58] Field of Search .......................................... 518/713

[56] References Cited

U.S. PATENT DOCUMENTS

| | | | |
|---|---|---|---|
| 1,741,308 | 12/1929 | Jaeger . | |
| 1,859,244 | 5/1932 | Patart . | |
| 2,061,470 | 11/1936 | Larson ................................ | 266/156 |
| 2,787,628 | 4/1957 | Himmler et al. . | |
| 3,901,664 | 8/1975 | Kozlowski et al. ..................... | 44/56 |

FOREIGN PATENT DOCUMENTS

| | | |
|---|---|---|
| 608361 | 1/1935 | Fed. Rep. of Germany . |
| 571356 | 5/1924 | France . |
| 16114 | 3/1927 | Netherlands . |
| 238319 | 8/1925 | United Kingdom . |
| 240955 | 10/1925 | United Kingdom . |
| 229715 | 2/1975 | United Kingdom . |
| 1159035 | 7/1985 | United Kingdom . |

OTHER PUBLICATIONS

Frolich, P. K. and Cryder, D. S., Ind. Eng. Chem. 1930, 22, 1051–1057.
Graves, G. D., Ind. Eng. Chem., 1931, 23, 1381–1385.
Morgan, G. T., Hardy, D. V. N., and Procter, R. H. J., Soc. Chem. Ind. Trans. Comm., 1932, 51, IT–7T.
Smith, K. J. and Anderson, R. B., Can. J. Chem. Eng., 1983, 61, 40–45.
Vedage, G. A., Himelfarb, P., Simmons, W. G., and Klier, K., "Alkali Promoted Cu/ZnO Catalysts for Low Alcohol Synthesis," Prepr. Petr. Div. ACS., Aug., 1983, Wash., D.C., pp. 1261–1271.
Negishi, R.; Rev. Phys. Chem. Japan, 15, 171–181 (1941).
Negishi, R.; Rev. Phys. Chem. Japan, 18, 47–57; and 58–70 (1944).
Cohn, E. M.; "Catalysis", (Emmett, P. H., Ed.), vol. IV, p. 443–472, Reinhold New York (1956).
Natta, G. et al; "Catalysis", (Emmett, P.H., Ed.), vol. IV p. 443–472, Reinhold, New York (1957).
Philip, B. H. et al; Tetr. Lett., 15, 523–526 (1961).
Lundeen, A. J. et al; J. Amer. Chem. Soc., 85, 2180–2181 (1963).
Lundeen, A. J., et al; J. Org. Chem. 32, 3386–3389 (1967).
Dent, A. L. et al; J. Phys. Chem., 73, 3781–3790 (1969).
Davis, B. H. et al; J. Catal., 25, 81–92 (1972).
Canesson, P. et al; J. Catal., 42, 205–212 (1976).
Yamaguchi, T., et al; Chem. Lett., 677–678 (1976).
Mariquez, J. M. et al; J. Amer. Chem. Soc., 100, 7112–7114 (1978).
Sapienza, R. S. et al; "Fundamental Research in Homogeneous Catalysis", (M. Tsutsui, Ed.), vol. 3, pp. 179–197, Plenuma Press, New York (1978).

*Primary Examiner*—Howard T. Mars
*Attorney, Agent, or Firm*—Maky, Renner, Otto & Boisselle

[57] ABSTRACT

An alcohol mixture suitable for combining with gasoline is produced by contacting synthesis gas at elevated temperature and pressure with an oxide complex catalyst containing copper, thorium, an alkali metal and at least one other specific element.

8 Claims, No Drawings

PREPARATION OF ALCOHOLS FROM SYNTHESIS GAS

This application is a continuation of application Ser. No. 503,076, filed June 13, 1983 (now abandoned), which was a continuation of application Ser. No. 393,829, filed June 30, 1982 (now abandoned), which was a continuation of application Ser. No. 054,216, filed July 2, 1979 (now abandoned), which was a continuation of application Ser. No. 905,703, filed May 15, 1978 (now abandoned). The disclosures of these prior applications are incorporated herein by reference in their entirety.

BACKGROUND OF THE INVENTION

The present invention relates to a new process for making alcohol mixtures preferably containing no more than 85% methanol and to gasoline compositions containing such alcohol mixtures.

It is well known to incorporate methanol into gasoline for the purpose of increasing the amount of useful fuel obtained. Unfortunately, the presence of a small amount of water in a methanol/gasoline mixture causes separation of the methanol and gasoline phases. In order to overcome this problem, higher alcohols can be added to methanol/gasoline mixtures, such compositions being able to tolerate a much greater amount of water than a simple methanol/gasoline mixture. See U.S. Pat. Nos. 3,832,149, 3,822,119 and 2,128,910. Higher alcohols can also be used alone. See U.S. Pat. No. 2,078,736.

Although it has been known for many years that alcohols can be incorporated into gasolines, most gasolines made at this time contain no alcohols, and this is due primarily to economic reasons.

It has also been long known to prepare alcohols by catalytically reacting carbon monoxide and hydrogen together using catalysts which may contain copper and thorium. See, for example, U.S. Pat. Nos. 1,707,331, 2,061,470, 2,500,913, 1,741,307, 1,625,929 and 1,831,179. Such processes, however, normally require extremely high reaction temperatures and pressures and hence have not been employed commercially to any significant extent.

Accordingly, it is an object of the present invention to provide a simple, straightforward and very inexpensive process for producing alcohol mixtures for incorporating into gasoline.

In addition, it is a further object of the present invention to provide a novel alcohol mixture and in addition a gasoline composition containing this novel alcohol mixture.

SUMMARY OF THE INVENTION

These and other objects are accomplished by the present invention in accordance with which a mixture of methanol and higher alcohols is produced by contacting synthesis gas with a novel copper/thorium/alkali metal oxide catalyst. Alcohol compositions produced by this procedure contain a unique distribution of alcohols having 2 to 6 carbon atoms and normally not more than 85% methanol by weight. These compositions can be directly admixed with gasoline to provide a new gasoline composition containing a mixed alcohol system which will not separate from the remainder of the gasoline even in the presence of significant amounts of water.

Thus, the present invention provides a unique process for producing alcohol mixtures, the inventive process comprising contacting a gaseous reactant containing carbon monoxide and hydrogen with an oxide complex catalyst described by the formula

$$Cu_a Th M_b A_c O_x$$

wherein
M is one or more of Ca, Mo, Rh, Mn, Pt, Ce, Cr, Zn, Al, Ti, La, V, U, Ru, Re and Pd;
A is an alkali metal; and
wherein
a is 0.5 to 2.5;
b is 0.01 to 1.0;
c is 0.05 to 0.9; and
x is a number such that the valence requirements of the other elements for oxygen is satisfied.

In addition, the present invention further provides a novel alcohol composition suitable for admixing with gasoline, the alcohol composition being composed of $C_2$ and higher alcohols having an alcohol distribution as follows:

$C_2$—4–25%
$C_3$—0.1–25%, preferably 9–25%
$C_4$—0.5–70%, preferably 40–70%
$C_5$—0.1–12%
$C_6$—0.1–10%
$C_6$—0.1–10% the percents being based on the weight of the total amount of alcohols in the mixture having two or more carbon atoms. Normally, this alcohol composition will also contain methanol, usually in amounts of 40 to 85% although the methanol content may range from 0 to 92% or more.

Furthermore, the present invention also provides a novel alcohol/gasoline composition comprising a homogenous solution of gasoline and the novel alcohol composition of the present invention.

DETAILED DESCRIPTION

Reactants

The material being reacted in accordance with the present invention to form alcohols is preferably synthesis gas. As is well known, synthesis gas is composed basically of a mixture of hydrogen and carbon monoxide in which the $H_2/CO$ ratio is from 0.6 to 6, more normally between 1 and 2. It is normally derived by heating coke in the presence of air and then steam. Alternately, it can also be produced by partial combustion of coal, natural gas or petroleum hydrocarbons. It is sometimes referred to as "water gas." Synthesis gas normally contains a very low amount of sulfur compounds. It also may contain small amounts of carbon dioxide, nitrogen and other inerts.

Although synthesis gas is a preferred reactant, any other gas composed primarily of hydrogen and carbon monoxide and having an $H_2/CO$ ratio of 0.6 to 6 can be employed. The gaseous reactant should contain as little sulfur compounds as possible since sulfur is a known poison for copper containing catalysts when used in conventional methanol synthesis. Preferably the gaseous reactant is essentially sulfur-free.

Reaction Mode and Conditions

The inventive process is carried out by contacting the gaseous reactant with the inventive catalyst as described below in a suitable reactor. The reaction can be carried out either in fluid-bed mode or fixed-bed mode, continuously or in batch operation.

The contact time of the reactants with the products is not critical but should be below about 200 seconds and preferably between about 35 and 135 seconds.

The reaction pressure should normally be between 500–1500 psi and is preferably between 750–1000 psi. Although there is no real upper limit to the reaction pressure, pressures higher than 1500 psi are normally not employed because of the high expense involved. Also, pressures as low as 250 psi can be employed, although it is preferable to operate at at least about 500 psi because formation of alcohols is favored at higher pressures.

The reaction temperature should be maintained between about 200°–425° C., preferably 250°–350° C., and most preferably 280°–330° C. The reaction temperature, like the reaction pressure, is not particularly critical, although a marked decrease in conversion rates will be obtained if temperatures and pressures lower than 250 psi and 200° C. are employed. Also, the amount of methanol in the reaction product increases with practically all catalysts when the reaction temperature drops below about 200° C. It will be noted that temperatures and pressures employed in this process are quite a bit lower than temperatures and pressures necessary in prior art processes for producing mixed alcohols from synthesis gas.

Catalyst

The catalyst employed in the inventive process is believed to be an oxide complex and can be described by the empirical formula:

$Cu_aThM_bA_cO_x$ wherein

M is one or more of Ca, Mo, Rh, Mn, Pt, Ce, Cr, Zn, Al, Ti, La, V, U, Ru, Re or Pd, preferably Cr, Zn, Al, Ti, La, V or Pd;

A is an alkali metal, preferably Na; and wherein a is 0.5 to 2.5, preferably 1.3 to 1.7;
b is 0.01 to 1.0, preferably 0.01 to 0.6;
c is 0.05 to 0.9, preferably 0.225 to 0.55; and
x is a number such that the valence requirements of the other elements for oxygen is satisfied.

These catalysts can be prepared by a procedure involving adding an alkali metal carbonate to an aqueous solution containing decomposable salts of thorium, copper and the "M" element, to form a precipitate heating the precipitate in its mother liquor for a suitable time, neutralizing the precipitate, drying the precipitate and thereafter calcining and then reducing the precipitate.

More specifically, the catalysts of the present invention can be prepared by the following procedure:

(1) A solution preferably aqueous, containing decomposable salts of thorium, copper and the "M" element is first formed. Nitrates are preferably used as the decomposable salts, although salts having other decomposable anions such as acetates, propionates, benzoates, acetyl acetonates, naphthenates, chlorides and the like can be employed.

(2) To the aqueous salt solution is added alkali metal carbonate, preferably also in the form of an aqueous solution. During this addition, the admixture is preferably maintained at an elevated temperature, e.g. 80°–95° C. As the alkali metal carbonate is added to the salt solution, carbon dioxide is evolved and a sky-blue precipitate whose exact nature is unknown begins to form. Addition of alkali metal carbonate is continued while maintaining the temperature of the system preferably between 80°–95° C. until the pH of the system, which is initially at about 1, increases to at least 7.5, preferably at least 8, preferably about 9.3–10. At this time a gelatinous sky-blue precipitate in significant amount has been formed. An alkali metal hydroxide can be used in place of the carbonate, although the carbonate is preferred because it gives better results.

(3) This gelatinous precipitate is then allowed to digest in its mother liquor while the temperature of the system is maintained at its elevated value, preferably 80°–95° C. During this time, it will be noted that the color of the precipitate undergoes a significant change from sky-blue through green through brown to nearly black.

(4) When no more color change occurs, an acid, preferably nitric acid, is added to bring the pH to about neutral, preferably 6.8–7, which is believed to cause precipitation of any dissolved Cu remaining in the mother liquor. The precipitate is then filtered and washed with water until the alkali metal content of the finished catalyst falls to the desired value. This can be easily determined by trial and error.

(5) The precipitate is then dried at a convenient temperature, for example 120° C., and then calcined for a time and at a temperature sufficient to drive out the remaining water in the precipitate and decompose decomposable ions remaining in the precipitate, such as nitrates and carbonates. Temperatures of 250°–500° C., preferably 350°–450° C. for periods of 30 minutes to about 5 hours have been found sufficient for this purpose.

(6) Since the catalyst of the present invention is used in a reducing atmosphere, it is preferable to reduce the calcined precipitate prior to use in the inventive process. Prereduction of the catalyst, however, is not necessary, since the catalyst will automatically undergo reduction to an equilibrium value in use, although the activity of the catalyst may not be as great as when a proper prereduction procedures is carried out. In this regard, it is believed that heating of the calcined precipitate to higher temperatures will cause significant reduction in the activity of the ultimate catalyst produced due to sintering of particles of the calcined precipitate. Since a very exothermic reaction may occur when a reducing gas is contacted with the calcined precipitate, it is preferable to subject the calcined precipitate to a controlled reduction procedure in order to avoid heating the calcined precipitate to above 300° C. Therefore, it is preferable to carry out a controlled reduction of the calcined precipitate in the following manner, although any other satisfactory technique could be employed as well.

The calcined precipitate is first heated under inert atmosphere preferably in the alternate reaction vessel to a temperature of about 200° C. Next, an inert gas containing a low concentration (e.g. about 5%) of a reducing gas, preferably $H_2$ although a mixture of $H_2$ and CO can be employed, is admitted to the gas surrounding the catalyst for initial reduction of the metal and concomitant heat evolution. Thereafter, the concentration of the reducing gas is slowly increased to 100%, care being taken to keep the rate of reducing gas applied low enough to prevent the temperature of the catalyst from exceeding a value at which significant sintering occurs, usually about 300° C. Once 100% reducing gas is reached, the pressure in the reaction vessel is slowly increased to the desired reaction pressure, the catalyst new being ready to receive reactant.

The catalysts of the present invention can be used alone or supported on various inert supports such as silica, alpha-alumina, Alundum, mullite and the like. These materials are preferably low surface area supports and can be added to the catalyst during its preparation (i.e. after the sky-blue precipitate is first formed) or after the preparation of the catalyst in conventional manners.

Product

The composition produced by the inventive process is a mixture of alcohols containing methanol predominantly as well as significant amount of higher alcohols usually having 2–8 carbon atoms. Normally, the alcohol product of the present invention will contain 40–85% methanol, although higher amounts of methanol may be included in the product if reaction temperature is too low, if the catalyst is calcined at too high a temperature or if the catalyst contains additional elements fostering the generation of higher amounts of methanol than normal.

In this regard, it has been found that the amount of methanol in the product alcohol mixture will usually exceed 85% if the M element in the catalyst is chosen as Ca, Mo, Rh, Mn, Pt, Re, Ru or in some instances Ce. For this reason, Cr, Zn, Al, Ti, La, V and Pd are preferred as the M element. In any event, an alcohol mixture produced by the inventive process and containing over 85% methanol can also be directly added to gasoline as is. It is preferable, however, to distill off excess methanol so that the methanol content of the alcohol mixture is no more than 85%.

The portion of the alcohol product other than methanol is a mixture composed substantially completely of 2–6 carbon atom alcohols. This $C_2$–$C_6$ alcohol mixture has an alcohol distribution scheme as given in the following Table I.

TABLE I $C_2$—4–25%
$C_3$—0.1–25%, preferably 9–25%
$C_4$—0.5–70%, preferably 40–70%
$C_5$—0.1–12%
$C_6$—0.1–10%
$C_6$—0.1–10% the percents being based on the weight of the total amount of alcohols in the products having 2 or more carbon atoms. These alcohols are composed almost completely of isoalcohols and normal alcohols with the iso/normal ratio being about 0.7 to 2. Substantially no tertiary alcohols are present.

Gasoline

The product alcohol mixtures of the present invention (whether containing more or less than 85% methanol) are useful in expanding gasoline. They can be mixed with gasoline in any amount, and when present in amounts of less than 25% no significant effect on the operation of an internal combustion engine containing the gasoline/alcohol mixture will be noticed. Furthermore, the mixed alcohol products of the present invention can be mixed with any type of gasoline be it substantially all paraffinic such as alkylate or highly aromatic. Moreover, if the product alcohol mixture employed has no more than 85% methanol, the resultant gasoline will be able to tolerate significant amounts of water without phase separation.

SPECIFIC EMBODIMENTS

In order to more thoroughly describe the present invention, the following specific examples are provided.

Catalyst Preparation

EXAMPLE 1

$Cu_{1.5}ThPd_{0.05}Na_yO_x$

To 660 cc of distilled water were added 60.66 grams of $Cu(NO_3)_2.2\frac{1}{2}H_2O$ and 95.99 grams of $Th(NO_3)_4.4H_2O$. The nitrates were dissolved by warming with stirring, and then 1.54 grams of $PdCl_2$ were disolved in the nitrate solution. The nitrate solution was heated to 90° C., and with high speed stirring there was added a hot (90°–95° C.) solution of 73.2 grams of $Na_2CO_3$ in 800 cc of distilled $H_2O$. Using a pH meter, sufficient additional $Na_2CO_3$ was added to bring the pH of the slurry to 9.5. Heating was continued until the color change to dark brown was complete, about half of the water being evaporated. The slurry was then cooled to room temperature, and the pH adjusted to 7.0 with a 20% $HNO_3$ solution. The slurry was filtered using vacuum, and sucked as dry as possible. The filter cake was washed three times by re-slurrying in 800 cc of distilled $H_2O$ at 60°–70° C., and refiltering. It was then dried approximately 16 hours at 120° C., and calcined 3 hours at 275° C. and 16 hours at 350° C. in air. The sodium content of the finished catalyst was 1.6 weight %.

EXAMPLE 2

$Cu_{1.5}ThCr_{0.3}Na_yO_x$

The procedure of Example 1 was followed except that 20.9 grams of $Cr(NO_3)_3.9H_2O$ rather than 1.54 grams $PdCl_2$ was dissolved in the copper-thorium nitrate solution. The final catalyst contained 0.55 weight % Na.

EXAMPLE 3

$Cu_{1.5}ThLa_{0.15}Na_yO_x$

The procedure of Example 1 was followed except that 11.3 grams of $La(NO_3)_3.6H_2O$ rather than the $PdCl_2$ was added to the copper-thorium nitrate solution. In addition, the final catalyst contained 1.45 weight % Na.

EXAMPLE 4

$Cu_{1.15}ThCe_{0.30}Na_yO_x$

The procedure of Example 1 was followed except that 22.6 grams of $Ce(NO_3)_3.6H_2O$ rather than the $PdCl_2$ was added to the copper-thorium nitrate solution. In addition, the catalyst contained 0.9 weight % Na.

EXAMPLE 5

$Cu_{1.5}ThTi_{0.15}Na_yO_x$

The procedure of Example 1 was followed except that in place of the $PdCl_2$ 2.1 grams of $TiO_2$ were suspended in the copper-thorium nitrate solution before precipitation. The catalyst contained 0.68% Na.

EXAMPLE 6

$Cu_{1.5}ThZn_{0.15}Na_yO_x$ 78 grams of $Cu(C_2H_3O_2)_2.H_2O$, 144 grams of $Th(NO_3)_4.4H_2O$ and 4.78 grams of ZnO in 1 liter of water were heated to 90° C. Precipitation was done with a hot solution of 117.3 grams $Na_2CO_3$ in 1.2 liters of $H_2O$. The pH was adjusted to 9.8 with additional $Na_2CO_3$. The balance of the preparation was accomplished in the same manner as set forth above in connection with Example 1.

EXAMPLE 7

$Cu_{1.5}ThAl_{0.15}Na_yO_x$

In 1 liter of distilled water were dissolved 94.5 grams $Cu(NO_3)_2.3H_2O$, 144 grams of $Th(NO_3)_4.4H_2O$ and 22.0 grams of $Al(NO_3)_3.9H_2O$, and the solution was heated to 90° C. This was added to a solution of 170.4 grams of $Na_2CO_3$ in 1.2 liters of distilled $H_2O$ and heated to 90°–95° C. The pH of the slurry was adjusted to 9.5 with additional $Na_2CO_3$. The remainder of the preparation was carried out in the same manner as set forth above in connection with Example 1. The catalyst contained 1.47 weight % Na.

EXAMPLE 8

$Cu_{1.0}Th_{1.0}Pd_{0.05}Na_yO_x$

The procedure of Example 1 was repeated except that 1.95 grams of $Pd(C_3H_8O_2)_2$ were employed in place of the $PdCl_2$ of Example 1. Also, the sodium content of the catalyst obtained was 1.28 weight %.

EXAMPLE 9

$Cu_{1.0}Th_{1.0}U_{0.2}Na_yO_x$

The procedure of Example 1 was repeated using 58.9 grams $Cu(NO_3)_2.3H_2O$, 134.6 grams $Th(NO_3)_4.4H_2O$ and 24.5 grams $(UO_2)(NO_3)_2.6H_2O$ dissolved in 600 cc of water to form the aqueous salt solution. The catalyst contained 1.6% Na.

EXAMPLE 10

$CuThCr_{0.15}Na_yO_x$

The procedure of Example 1 was repeated except that 94.5 g $Cu(NO_3)_2.3H_2O$, 144 g $Th(NO_3)_4.4H_2O$ and 23.5 g $Cr(NO_3)_3.9H_2O$ in distilled water were used and in addition 119.1 gm $Na_2CO_3$ in 1 liter of water was used. The catalyst obtained contained 1.0% Na.

EXAMPLE 11

$CuThCe_{0.15}Na_yO_x$

The procedure of Example 10 was repeated except that 25.5 gm $Ce(NO_3)_3.6H_2O$ and 120 gm $Na_2CO_3$ in 2 liters water were used. The catalyst contained 1.21% Na.

Alcohol Production

EXAMPLES 12 TO 22 AND COMPARATIVE EXAMPLES A AND B

A series of experiments was run in order to determine the catalytic activity of the various catalysts prepared in Examples 1–11 in the production of alcohol mixtures. In each experiment, 40 cc of catalyst was charged into a fixed-bed reactor and contacted with an $H_2/CO$ mixture having an $H_2/CO$ ratio of approximately 1/1. The processes were carried out at a temperature of 288° C., a pressure of 750 psig and a contact time of 52 seconds. The results obtained are tabulated in the following Tables II and III.

EXAMPLES 23 TO 33

Additional experiments were conducted using the same conditions as in Examples 12 to 22. The catalysts used in these experiments are described by the general formula.

$$Cu_{1.5}ThM_bNaO_x$$

with the $M_b$ member of each catalyst and the results obtained being set forth in the following Table IV.

TABLE II

| | | Percent Yield of Methanol and Higher Alcohols | | | | |
|---|---|---|---|---|---|---|
| | | % Yield* | | Product Composition (Wt.%) | | |
| Example | Catalyst Composition | Alcohols | $CO_2$ | MeOH | $C_{2+}$ Alcohols | $C_1/C_{2+}$ Alcohol Ratio |
| 12 | $Cu_{1.5}ThPd_{0.05}Na_yO_x$ | 19.2 | 11.3 | 67.1 | 30.7 | 2.2 |
| 13 | $Cu_{1.5}ThCr_{0.3}Na_yO_x$ | 16.5 | 10.9 | 83.5 | 15.0 | 5.6 |
| 14 | $Cu_{1.5}ThLa_{0.15}Na_yO_x$ | 15.9 | 10.9 | 83.4 | 15.6 | 5.3 |
| 15 | $Cu_{1.5}ThCe_{0.3}Na_yO_x$ | 16.1 | 13.3 | 75.8 | 23.1 | 3.3 |
| 16 | $Cu_{1.5}ThTi_{0.15}Na_yO_x$ | 15.3 | 11.0 | 84.4 | 15.3 | 5.5 |
| 17 | $Cu_{1.5}ThZn_{0.15}Na_yO_x$ | 17.1 | 9.0 | 77.7 | 18.1 | 4.3 |
| 18 | $Cu_{1.5}ThAl_{0.15}Na_yO_x$ | 13.9 | 9.1 | 84.0 | 15.1 | 5.6 |
| 19 | $Cu_{1.5}ThPd_{0.05}Na_yO_x$ | 19.5 | 11.5 | 64.6 | 33.0 | 2.0 |
| 20 | $Cu_{1.0}ThU_{0.2}Na_yO_x$ | 4.91 | 3.34 | 91.5 | 8.5 | |
| 21 | $Cu_{1.5}ThCr_{0.15}Na_yO_x$ | 15.8 | 8.6 | 78.8 | 21.1 | 3.7 |
| 22 | $Cu_{1.5}ThCe_{0.15}Na_yO_x$ | 17.4 | 9.8 | 77.8 | 21.1 | 3.7 |
| A | $Cu_{0.51}ZnAl_{0.760}O_x$ (commercial MeOH catalyst) | 14.4 | 7.3 | 93.5 | 5.9 | 15.8 |
| B | $Cu_{0.51}ZnAl_{0.760}$ + 2.5% Na | 15.9 | 5.8 | 93.4 | 6.3 | 14.8 | insert

TABLE III

| | Distribution of Alcohols in Product | | | | | | | | | | |
|---|---|---|---|---|---|---|---|---|---|---|---|
| Experiment No. | 12 | 13 | 14 | 15 | 16 | 17 | 18 | 19 | 20 | 21 | 22 |
| $M_b$ | $Pd_{0.05}$ | $Cr_{0.3}$ | $La_{0.15}$ | $Ce_{0.3}$ | $Ti_{0.15}$ | $Zn_{0.15}$ | $Al_{0.15}$ | $Pd_{0.05}$ | $U_{0.2}$ | $Cr_{0.15}$ | $Ce_{0.15}$ |
| Liquid Analysis, Wt. % | | | | | | | | | | | |
| methanol | 67.1 | 83.5 | 83.4 | 75.8 | 84.4 | 77.7 | 84.0 | 64.6 | 92.2 | 78.8 | 77.8 |
| ethanol | 3.5 | 1.7 | 1.8 | 1.1 | 1.2 | 2.7 | 2.4 | 3.1 | 1.9 | 1.8 | 1.5 |

TABLE III-continued

| | Distribution of Alcohols in Product | | | | | | | | | | |
|---|---|---|---|---|---|---|---|---|---|---|---|
| Experiment No. | 12 | 13 | 14 | 15 | 16 | 17 | 18 | 19 | 20 | 21 | 22 |
| acetone | 0.4 | 0.5 | 0.5 | — | 0.6 | 0.3 | 0.4 | 0.7 | — | 0.6 | 0.6 |
| iso-$C_3OH$ | 1.0 | 0.5 | 0.6 | 1.3 | 0.4 | 0.7 | 0.7 | 0.9 | 0.1 | 0.7 | 0.7 |
| n-$C_3OH$ | 4.7 | 1.4 | 1.5 | 0.9 | 0.9 | 1.6 | 2.1 | 3.9 | 0.4 | 2.3 | 1.6 |
| sec-$C_4OH$ | 0.7 | 1.1 | 0.7 | 1.5 | 1.1 | 0.4 | 0.6 | 1.3 | — | 0.9 | 1.1 |
| iso-$C_4OH$ | 12.2 | 6.8 | 7.0 | 13.6 | 8.4 | 7.3 | 6.4 | 15.2 | 0.5 | 10.6 | 10.9 |
| n-$C_4OH$ | 2.2 | 1.3 | 1.3 | 1.8 | 1.3 | 1.4 | 0.7 | 2.6 | 0.04 | 1.3 | 1.7 |
| iso-$C_5OH$ | 0.7 | 0.1 | 0.2 | — | trace | 0.5 | 0.4 | 0.5 | 0.06 | 0.8 | 0.4 |
| n-$C_5OH$ | 2.8 | 0.7 | 1.2 | 1.7 | trace | 1.7 | 1.1 | 2.4 | 0.07 | 1.3 | 1.2 |
| iso-$C_6OH$ | 0.5 | 0.2 | 0.2 | 0.1 | 0.8 | 0.3 | 0.1 | 0.5 | — | 0.2 | 0.3 |
| n-$C_6OH$ | 1.8 | 0.7 | 0.8 | 1.2 | 0.5 | 1.2 | 0.3 | 2.1 | 0.1 | 0.9 | 1.1 |
| —$C_6AlC$ | 2.4 | 1.5 | 0.8 | 1.1 | 0.4 | 4.2 | 0.8 | 2.2 | 4.6 | 0.2 | 1.1 |
| $M_b$ | $Pd_{0.05}$ | $Cr_{0.3}$ | $La_{0.15}$ | $Ce_{0.3}$ | $Ti_{0.15}$ | $Zn_{0.15}$ | $Al_{0.15}$ | $Pd_{0.05}$ | $U_{0.2}$ | $Cr_{0.15}$ | $Ce_{0.15}$ |
| Weight %, MeOH Free Basis | | | | | | | | | | | |
| ethanol | 10.64 | 10.3 | 10.84 | 4.55 | 7.69 | 11.80 | 15.0 | 8.76 | 24.5 | 8.50 | 6.76 |
| acetone | 1.22 | 3.03 | 3.01 | — | 3.84 | 1.32 | 2.50 | 1.98 | — | 2.83 | 2.70 |
| iso-$C_3OH$ | 3.04 | 3.03 | 3.62 | 5.37 | 2.57 | 3.09 | 4.38 | 2.54 | 1.3 | 3.31 | 3.15 |
| n-$C_3OH$ | 14.29 | 8.48 | 9.03 | 3.72 | 5.77 | 7.05 | 13.13 | 11.03 | 0.4 | 10.85 | 7.21 |
| sec-$C_4OH$ | 2.13 | 6.67 | 4.22 | 6.20 | 7.04 | 1.77 | 3.75 | 3.67 | — | 4.25 | 4.96 |
| iso-$C_4OH$ | 37.10 | 41.20 | 42.20 | 56.20 | 53.90 | 32.20 | 40.00 | 43.00 | 6.4 | 50.00 | 49.20 |
| n-$C_4OH$ | 6.68 | 7.88 | 7.83 | 7.43 | 8.33 | 6.17 | 4.38 | 7.34 | 0.5 | 6.07 | 7.66 |
| iso-$C_5OH$ | 2.13 | 0.61 | 1.20 | — | trace | 2.22 | 2.50 | 1.41 | 0.8 | 3.77 | 1.80 |
| n-$C_5OH$ | 8.52 | 4.25 | 7.22 | 7.02 | trace | 7.48 | 6.88 | 6.78 | 0.9 | 6.13 | 5.40 |
| iso-$C_6OH$ | 1.52 | 1.21 | 1.20 | 0.41 | 5.12 | 1.32 | 0.63 | 1.41 | — | 0.94 | 1.35 |
| n-$C_6OH$ | 5.48 | 4.25 | 4.82 | 4.95 | 3.21 | 5.28 | 1.88 | 5.93 | 1.3 | 4.25 | 4.96 |
| —$C_6AlC$ | 7.29 | 9.10 | 4.82 | 4.54 | 2.57 | 18.50 | 5.00 | 6.22 | 59.1 | 0.94 | 4.96 |
| Iso/Normal Ratio | | | | | | | | | | | |
| $C_3$ | .213 | .357 | .401 | 1.44 | .445 | .438 | .333 | .230 | 3.25 | .305 | .437 |
| $C_4$ | 5.55 | 6.33 | 5.40 | 7.57 | 6.48 | 5.22 | 9.13 | 5.85 | 12.8 | 8.23 | 6.43 |
| $C_5$ | 0.250 | 0.144 | 0.166 | — | 0.297 | 0.363 | 0.208 | 0.89 | 0.615 | 0.333 | |
| $C_6$ | 0.277 | 0.285 | 0.249 | 0.083 | 1.59 | 0.250 | 0.335 | 0.238 | — | 0.221 | 0.272 |
| overall | 0.917 | 1.101 | 1.097 | 1.830 | 1.922 | 0.982 | 1.055 | 1.111 | 2.75 | 1.449 | 1.502 |

TABLE IV

| Experiment No. | 23 | 24 | 25 | 26 | 27 | 28 | 29 | 30 | 31 | 32 | 33 |
|---|---|---|---|---|---|---|---|---|---|---|---|
| $M_b$ | $Ca_{0.15}$ | $Mo_{0.15}$ | $Rh_{0.025}$ | $Ce_{0.5}$ | $Ce_{0.75}$ | $Mn_{0.15}$ | $V_{0.15}$ | $Ru_{0.05}$ | $Rh_{0.05}$ | $Re_{0.05}$ | $Pt_{0.05}$ |
| Liquid Analysis, Weight % | | | | | | | | | | | |
| methanol | 84.40 | 86.58 | 87.78 | 86.23 | 89.02 | 85.52 | 91.30 | 92.02 | 90.95 | 91.09 | 88.40 |
| ethanol | 1.44 | 1.59 | 1.69 | 1.55 | 2.57 | 1.83 | 1.09 | 2.95 | 2.11 | — | 2.45 |
| acetone | 0.22 | — | 0.12 | 0.25 | 0.21 | 0.38 | 0.41 | 0.96 | — | 0.84 | 0.18 |
| iso-$C_3OH$ | 0.67 | 0.64 | 0.47 | 0.46 | 0.53 | 0.63 | 0.44 | — | 0.43 | 1.38 | 0.51 |
| n-$C_3OH$ | 1.26 | 1.42 | 1.58 | 1.96 | 2.45 | 1.43 | 0.82 | 1.11 | 1.36 | 0.25 | 2.01 |
| sec-$C_4OH$ | 0.50 | 0.31 | 0.16 | 0.33 | 0.21 | 0.53 | 0.59 | 0.17 | 0.18 | 0.64 | 0.21 |
| iso-$C_4OH$ | 6.32 | 6.31 | 5.64 | 6.60 | 3.07 | 6.05 | 4.41 | 1.29 | 3.47 | 0.49 | 3.74 |
| n-$C_4OH$ | 0.87 | 1.07 | 0.87 | 0.99 | 0.58 | 1.38 | 0.18 | — | 0.49 | 1.34 | 0.73 |
| iso-$C_5OH$ | 0.37 | 0.22 | 0.05 | — | 0.07 | — | 0.15 | 0.18 | 0.06 | — | 0.18 |
| n-$C_5OH$ | 0.70 | 0.94 | 0.77 | 0.85 | 0.42 | 0.97 | 0.17 | 0.09 | 0.43 | 1.13 | 0.67 |
| iso-$C_6OH$ | 0.23 | 0.20 | 0.09 | 0.10 | 0.02 | — | 0.12 | 0.10 | 0.15 | 0.62 | 0.13 |
| n-$C_6OH$ | 0.32 | 0.57 | 0.52 | 0.50 | 0.22 | 0.56 | 0.05 | 0.07 | 0.23 | 1.34 | 0.36 |
| $C_6AlC$ | 2.70 | 0.15 | 0.26 | 0.19 | 0.63 | 0.73 | 0.27 | 1.07 | 0.15 | 0.90 | 0.43 |
| Weight %, MeOH Free Basis | | | | | | | | | | | |
| ethanol | 9.23 | 11.85 | 13.83 | 11.26 | 23.41 | 12.64 | 12.53 | 36.97 | 23.31 | — | 21.12 |
| acetone | 1.41 | — | 0.98 | 1.82 | 1.91 | 2.62 | 4.71 | 12.03 | — | 9.43 | 1.55 |
| iso-$C_3OH$ | 4.29 | 4.77 | 3.85 | 3.34 | 4.83 | 4.35 | 5.06 | — | 4.75 | 15.49 | 4.40 |
| n-$C_3OH$ | 8.08 | 10.58 | 12.93 | 14.23 | 22.31 | 9.88 | 9.43 | 13.91 | 15.03 | 2.81 | 17.33 |
| $M_b$ | $Ca_{0.15}$ | $Mo_{0.15}$ | $Rh_{01025}$ | $Ce_{0.5}$ | $Ce_{0.75}$ | $Mn_{0.15}$ | $V_{0.15}$ | $Ru_{0.05}$ | $Rh_{0.05}$ | $Re_{0.05}$ | $Pt_{0.05}$ |
| sec-$C_4OH$ | 3.21 | 2.31 | 1.31 | 2.40 | 1.91 | 3.66 | 6.78 | 2.13 | 1.99 | 7.18 | 1.81 |
| iso-$C_4OH$ | 40.51 | 47.02 | 46.15 | 47.93 | 27.96 | 41.78 | 50.69 | 16.16 | 38.34 | 5.58 | 32.24 |
| n-$C_4OH$ | 5.58 | 7.97 | 7.12 | 3.52 | 5.28 | 9.53 | 2.07 | — | 5.51 | 15.04 | 6.29 |
| iso-$C_5OH$ | 2.37 | 1.67 | 0.41 | — | 0.64 | — | 1.72 | 2.26 | 0.66 | — | 1.55 |
| n-$C_5OH$ | 4.49 | 7.00 | 6.30 | 6.17 | 3.82 | 6.70 | 1.95 | 1.13 | 4.75 | 12.68 | 5.78 |
| iso-$C_6OH$ | 1.47 | 1.49 | 0.74 | 0.73 | 0.18 | — | 1.38 | 1.25 | 1.66 | 6.96 | 1.12 |
| n-$C_6OH$ | 2.05 | 4.25 | 4.26 | 3.63 | 2.00 | 3.87 | 0.57 | 0.88 | 2.54 | 15.04 | 3.10 |
| $C_6AlC$ | 17.31 | 1.11 | 2.13 | 1.38 | 5.74 | 5.04 | 3.10 | 13.41 | 1.66 | 10.10 | 3.71 |
| iso/Normal Ratio | | | | | | | | | | | |
| $C_3$ | 0.531 | 0.451 | 0.298 | 0.235 | 0.216 | 0.440 | 0.537 | 0 | 0.316 | 5.51 | 0.254 |
| $C_4$ | 4.61 | 4.57 | 5.47 | 8.10 | 3.89 | 3.17 | 5.73 | 7.59 | 5.11 | 0.248 | 3.98 |
| $C_5$ | 0.528 | 0.239 | 0.065 | — | 0.167 | — | 0.882 | 2.97 | 0.139 | 0 | 0.268 |
| $C_6$ | 0.717 | 0.351 | 0.174 | 0.201 | 0.090 | — | 2.42 | 1.42 | 0.654 | 0.463 | 0.361 |
| overall | 1.490 | 1.250 | 1.118 | 1.262 | 0.572 | 0.997 | 1.766 | 0.358 | 0.855 | 0.530 | 0.709 |

From the foregoing, it can be seen that alcohol mixtures having a novel distribution of alcohols as described above are produced by a very simple and straightforward procedure. Each of these alcohol mixtures can be directly mixed with gasoline to provide novel alcohol/gasoline compositions, or, if desired, those alcohol mixtures containing more than 85% methanol can be fractionally distilled prior to admixing with gasoline to remove excess methanol.

Although only a few embodiments of the present invention have been described above, many modifications can be made without departing from the spirit and scope of the invention. All such modifications are intended to be included within the scope of the present invention which is to be limited only by the following claims.

We claim:

1. A process for producing a mixture of methanol and higher alcohols comprising contacting a gaseous reactant containing carbon monoxide and hydrogen at a temperature in the range of 250° to 350° C. and a pressure of no more than 1500 psi with an oxide complex catalyst described by the following empirical formula:

$$Cu_aTh M_b A_c O_x$$

wherein

M is one or more of Ca, Rh, Pt, Al, La, Re, Ru and Pd;

A is an alkali metal; and wherein a is 0.5 to 2.5;

b is 0.01 to 1.0;

c is 0.05 to 0.9; and x is a number such that the valence requirements of the other elements for oxygen is satisfied.

2. The process of claim 1 wherein the $H_2/CO$ ratio in said gaseous reactant is from 0.6–6.

3. The process of claim 1 wherein said gaseous reactant is synthesis gas.

4. The process of claim 1 wherein said reaction is carried out in fixed-bed mode.

5. The process of claim 1 wherein said oxide complex catalyst is prepared by the process comprising:

(1) adding an alkali metal carbonate or hydroxide to a solution containing decomposable salts of thorium, copper and "M" to raise the pH of the solution to at least 7.5 and form a precipitate, (2) heating the precipitate in its mother liquor until change in color of said precipitate has ceased, (3) neutralizing the mother liquor, (4) recovering the precipitate, and (5) calcining the precipitate in the presence of an oxygen-containing gas.

6. The process of claim 5 wherein the pH of the solution in (1) is raised to a pH of about 9.3 to about 10.

7. The process of claim 5 wherein a carbonate is added in step (1) of the catalyst preparation process, said catalyst preparation process further comprising:

(6) contacting said catalyst with a reducing gas while maintaining the temperature of said catalyst below the temperature at which significant sintering occurs.

8. The process of claim 1 wherein M is Al, La and/or Pd.

* * * * *